(12) United States Patent
Nandi et al.

(10) Patent No.: US 9,102,585 B2
(45) Date of Patent: Aug. 11, 2015

(54) EFFICIENT CONTINUOUS PROCESS FOR MANUFACTURING OF 4-AMINODIPHENYLAMINE FROM ANILINE AND NITROBENZENE

(75) Inventors: Chinmoy Nandi, Mumbai (IN); Narendra Gangal, Mumbai (IN); Pramod Purohit, Mumbai (IN); Vinay Ketkar, Mumbai (IN); Prahlad Rao, Mumbai (IN)

(73) Assignee: NOCIL LIMITED, Mumbai (IN)

( * ) Notice: Subject to any disclaimer, the term of this patent is extended or adjusted under 35 U.S.C. 154(b) by 0 days.

(21) Appl. No.: 14/391,419

(22) PCT Filed: Apr. 13, 2012

(86) PCT No.: PCT/IB2012/051829
§ 371 (c)(1),
(2), (4) Date: Oct. 9, 2014

(87) PCT Pub. No.: WO2013/153419
PCT Pub. Date: Oct. 17, 2013

(65) Prior Publication Data
US 2015/0038743 A1 Feb. 5, 2015

(51) Int. Cl.
*C07C 209/00* (2006.01)
*C07C 209/36* (2006.01)
*C07C 209/60* (2006.01)

(52) U.S. Cl.
CPC .............. *C07C 209/36* (2013.01); *C07C 209/60* (2013.01); *C07C 2523/44* (2013.01)

(58) Field of Classification Search
None
See application file for complete search history.

(56) References Cited

U.S. PATENT DOCUMENTS

| 5,117,063 A | 5/1992 | Stern et al. |
| 5,608,111 A | 3/1997 | Stern et al. |
| 5,739,403 A | 4/1998 | Reinartz et al. |
| 6,140,538 A * | 10/2000 | Rains et al. ............... 564/416 |
| 7,084,302 B2 | 8/2006 | Feng et al. |
| 7,176,333 B2 | 2/2007 | Wang et al. |
| 7,235,694 B2 | 6/2007 | Feng et al. |
| 7,989,662 B2 | 8/2011 | Feng et al. |
| 2012/0053367 A1 * | 3/2012 | Feng et al. ............... 564/422 |

OTHER PUBLICATIONS

Jurgen Gmehling et al., "Azeotropic Data, Part II" VCH Publishers, Inc., New York, NY 1994 (p. 1129) 3 pages.
Horsley, "Azeotropic Data—III" American Chemical Society, 1973 (p. 28) 3 pages.
Excerpts from "Chemical Reaction Engineering Third Edition" Department of Chemical Engineering Oregon State University, Published by John Wiley & Sons, 2001, pp. 90, 91, 94, and 101 (6 pages).
Excerpts from "Communications to the Editor" vol. 86, Mar. 5, 1964, pp. 960 and 961 (2 pages).
Musker, "Textbook Errors, 83 Nitrogen Ylides from Tetramethylammonium Salts" Journal of Chemical Education, vol. 45, No. 3, Mar. 1968, pp. 200-202 (3 pages).

* cited by examiner

*Primary Examiner* — Sudhakar Katakam
(74) *Attorney, Agent, or Firm* — Vincent J. Allen; Shaukat A. Karjeker; Carstens & Cahoon, LLP (57) ABSTRACT

An efficient continuous manufacturing process for 4-aminodiphenylamine by coupling aniline with nitrobenzene in the presence of tetramethylammonium hydroxide (TMAH) as a base, using flow reactors wherein base decomposition is considerably reduced by optimizing base quantity, process conditions and process equipment.

23 Claims, 1 Drawing Sheet

EFFICIENT CONTINUOUS PROCESS FOR MANUFACTURING OF 4-AMINODIPHENYLAMINE FROM ANILINE AND NITROBENZENE

FIELD OF INVENTION

The present invention relates to a continuous process for preparing 4-aminodiphenylamine by coupling aniline with nitrobenzene in the presence of tetramethylammonium hydroxide (hereinafter referred as TMAH) as a base using suitable continuous reactors. The present invention also relates to improved stability of TMAH in the presence of aniline and in particular in a coupling reaction product used for a 4-aminodiphenylamine manufacturing process.

PRIOR ART

4-Aminodiphenylamines are widely used as intermediates in the manufacture of their N-alkylated derivatives which have utility as antiozonants and antioxidants, as stabilizers for monomers and polymers, and in various specialty applications. For example, reductive alkylation of 4-aminodiphenylamine (hereinafter referred as 4-ADPA) with methyl isobutyl ketone provides N-(1,3-dimethylbutyl)-N'-phenyl-p-phenylenediamine (hereinafter referred as 6PPD), which is a useful antiozonant for the protection of various rubber products.

4-Aminodiphenylamines can be prepared in various ways. An economically attractive and green synthetic route is the coupling reaction of aniline with nitrobenzene in the presence of a base, specially TMAH, followed by catalytic hydrogenation of the reaction product in the presence of water, as disclosed, for example, in U.S. Pat. No. 5,117,063 (Stern et. al.; hereinafter "the '063 patent"), U.S. Pat. No. 5,608,111 (Stern et al., hereinafter "the '111 patent"), U.S. Pat. No. 5,739,403 (Reinartz et al.; hereinafter "the '403 patent") and U.S. Pat. No. 6,140,538 (Rains et al; hereinafter "the '538 patent").

The '111 patent describes a process for the preparation of an optionally substituted 4-ADPA wherein optionally substituted aniline and optionally substituted nitrobenzene are reacted in the presence of a base in a coupling reaction, followed by catalytic hydrogenation after addition of water to the coupling product. The hydrogenation catalyst, which typically is a supported noble metal catalyst, is removed from the hydrogenation reaction mixture, the organic phase is separated in order to isolate the 4-ADPA, and the aqueous phase, which contains the base, is returned to another cycle of the initial reaction mixture. In working examples, aniline and nitrobenzene are reacted in the presence of TMAH as a base, and water and aniline are azeotropically removed during the coupling reaction.

The '403 patent describes a process for a coupling reaction comparable to that of Example 13 of the '111 patent, followed by catalytic hydrogenation, where the amount of water added prior to hydrogenation is 25 to 80 wt. % relative to the weight of the coupling reaction mixture. Example 1 of the '403 patent is distinguished from Example 13 of the '111 patent on the basis that it requires a 4-hour hold period, with continued distillation for completion of the coupling reaction of aniline and nitrobenzene in presence of TMAH, after completion of nitrobenzene addition. After the hydrogenation, toluene is added, the catalyst is filtered, and the organic and aqueous phases are separated. In Example 1 of the '403 patent, it is stated that, "Analysis of the aqueous phase shows that 99.7% of the introduced tetramethylammonium hydroxide may be isolated. The resultant aqueous phase may be returned to the reaction without loss of reactivity."

The '538 patent teaches that by distilling out more aniline-water at the end of the coupling reaction, TMAH decomposition is substantially enhanced, and hence the process becomes economically unattractive. The '538 patent emphasizes the thermal stability of TMAH by highlighting a minimum moisture content requirement for the reaction mass at the start and end of the coupling reaction. Besides this aspect, most of the embodiments of the invention described in the '538 patent are similar to those of the earlier the '111 and '063 patents. Both the '111 and '538 patents describe formation of water-aniline azeotrope, in the distillation during the coupling reaction, see e.g. column 4 lines 10-39 of the '538 patent.

The '111 patent prescribes the water to base molar ratio at the start of the coupling reaction, but is silent about the water to base molar ratio at the end of the coupling reaction, though it specifies the modes of addition of nitrobenzene and removal of water aniline mixture during the coupling reaction stage; (see e.g. Example 13 of the '111 patent).

The '538 patent emphasizes that the water to base molar ratio at the end of the coupling reaction should be 0.3:1 as per Example 13 of the '111 patent and Example 1 of the '403 patent and acknowledges that there could be decomposition of the TMAH at this ratio. This conclusion, however, is not supported by experimental evidence but instead appears to be based on an assumption that during distillation, an aniline-water azeotrope of a fixed composition of water:aniline 86.4:13.6 w/w is removed as the distillate.

The literature provides information about the azeotropic compositions of aniline and water, as given in Table 1 (Azeotropic Data III, Compiled by Lee H. Horsley, Dow Chemical Co., Advances in Chemistry Series 116, American Chemical Society, Washington D.C., 1973, ISBN 841201668, pg 28):

TABLE 1

| Azeotropic compositions of aniline and water at different temperatures | |
|---|---|
| Temperature (° C.) | wt % of water in the azeotropic composition |
| 41 | 86.6 |
| 46 | 84.0 |
| 75 | 81.8 |
| 90 | 80.5 |

In another reference, the mole fraction of water in water—aniline azeotropic mixture at 99° C. is reported to be 0.96 (Azeotropic Data, by J. Gemhling, J. Menke, K. Fischer, J. Krafczyk, 1st Edition, Vol 2, page 1129, VCH Publishers Inc. New York, 1994, ISBN 3-527-28671-3). If this is converted to weight %, the composition comes out to be 82.3 weight % of water. This is relatively close to the values reported in Table 1. From Table 1, it is clear that the azeotropic composition contains 81.8% water by wt. at 75° C. and considering this value, the water to base molar ratio as per example 13 of the '111 patent at the end of coupling reaction is calculated to be about 0.6:1. Hence, calculation of the water to base molar ratio of example 13 of the '111 patent based on the assumption that the distillate is an azeotrope of aniline and water in the ratio of 86.4:13.6 is incorrect.

The innovation claimed in the '538 patent is that the water to base molar ratio should be not less than about 0.6:1 at the end of the coupling reaction, in order to avoid the decomposition of TMAH. The stability data of the Tetramethylammonium (hereinafter TMA) salts of 4-nitrosodiphenylamine (hereinafter "4-NODPA") and 4-nitrodiphenylamine (hereinafter "4-NDPA") is not provided in the '538 patent and does not appear to be available in literature for the experimental conditions of the '538 patent. Also the respective hydration states of 4-NODPA and 4-NDPA are also not mentioned. Thus, the water which is remaining at the end of the coupling reaction, the amount of the water that is bound with the TMAH and the amount of free water is not addressed. In the absence of this information, the decomposition of TMAH in the reaction mixture at the end of the coupling reaction cannot be conclusively determined.

It is well known in the literature that there are three basic types of reactors: (a) batch reactors, (b) plug flow reactors, and (c) mixed flow reactors (Chemical Reaction Engineering, O. Levenspiel, Third edition, John Wiley and Sons, 2001, ISBN 9971-512-41-6 page 90). The book explicitly states that: "In a batch reactor, the reactants are initially charged into a container, are well mixed, and are left to react for a certain period of time. The resultant mixture is then discharged. This is an unsteady state operation where composition changes with time". The plug flow reactor and mixed flow reactor are characterized by the fact that there is a continuous flow of both fluid reactants into the reactor and products out of the reactor. The plug flow reactor, as well as the mixed flow reactor, is operated at steady state (page 94, 101). This implies that compositions of streams going into the reactor and coming out of the reactor as well as at any point within the reactor do not change with time.

In the '538 patent it is mentioned that "The process steps of the present invention for the preparation of 4-aminodiphenylamines may be conducted as batch processes or they may be performed continuously using means and equipment well known to the skilled person." See col. 9, lines 52-54 of the '538 patent. Moreover the '538 patent defines the start and end of the process in terms of a "point in time." See col. 5, lines 43 and 46 of the '538 patent. This implies that process parameters, such as the composition within the reactor and the composition of the distillate change with time. As per the aforementioned description of batch vs. continuous processes, the process description given in the '538 patent and the corresponding claims are applicable to batch process only. Further, there are no working examples given in the '538 patent showing that the described process steps can be conducted in a continuous manner. Hence, this suggests that the results reported in the patent are applicable to batch processes.

U.S. Pat. Nos. 7,084,302, 7,176,333, 7,235,694 and 7,989,662 etc. describe preparation of 4-ADPA, in a continuous manner, by reacting aniline with nitrobenzene in the presence of a base and hydrogenating the mixture, followed by refining the reaction mixture. However, for coupling of aniline and nitrobenzene, complex base catalyst is used instead of TMAH. The complex base is defined as a mixture of a tetra alkyl ammonium hydroxide, an alkali metal hydroxide and a quaternary ammonium salt in various molar ratios. This complex base catalyst is said to be stable as compared to TMAH alone, particularly when there is a low water to base molar ratio at the end of coupling reaction. Also, as per the teachings of these patents that water content in the reaction mass is always relatively high and the water content is not carefully controlled in the coupling reaction. Moreover, instead of a noble metal catalyst, a powdery composite catalyst comprising nickel, aluminum and a transition metal such as Fe, Cu, Co etc. is used for hydrogenation of the aniline-nitrobenzene coupling product by employing a low temperature continuous reduction process. Decomposition of TMAH is not addressed in any of these steps.

One objective of the present invention is to develop a 4-ADPA process which will be of low capital cost, have a high process efficiency in terms of volume productivity and process consistency, based on the coupling reaction of aniline and nitrobenzene in the presence of TMAH.

Batch processes have the following distinct disadvantages: a) capital expenditure is high since the batch size decides the volume/size of equipment required for each unit operation; b) voluminous equipment also requires extensive civil work and complicated interconnecting piping; c) quality consistency requires very close process monitoring with a backup system of sophisticated process control and analytical instrumentation; d) high energy cost since each batch undergoes through heating and cooling cycles; e) high maintenance cost since each piece of equipment goes through repeated start/stop modes depending on the cycle time; f) low capacity utilization since the batch processes require "In between batches maintenance" and predictive maintenance of a batch process is difficult. Normally batch processes do not operate at >85% plant capacity. Hence, a batch process leads to higher variable cost of manufacturing and a reduced business advantage in comparison to a continuous process. On the other hand, one of the distinct advantages of a batch process is 100% conversion of raw materials to finished product. Theoretically, a continuous process requires infinite reactors in series to achieve 100% conversion. However, if the process need not to achieve 100% conversion in a reaction and the unconverted raw materials can be easily separated and recycled, without reducing process efficiency, significantly increasing unit cost and without detrimental effects on the final product quality, a continuous process is preferred over a batch process. A basic prerequisite, however, is that the reaction chemistry must permit adoption of continuous process.

In the development of a commercial process for manufacture of 4-ADPA, using a coupling reaction of aniline with nitrobenzene in the presence of TMAH, it was found by the inventors that a continuous process can be employed to significantly increase the volume productivity of the process, relative to the corresponding batch process and thus that a batch process and requires very large reactors in the coupling and subsequent basic reduction steps.

Also, the coupling of aniline with nitrobenzene in the presence of TMAH produces phenazine and azobenzene as by-products. Azobenzene can be reduced to aniline by catalytic hydrogenation and then can be recycled to the process. However, phenazine, is a troublesome by-product which poses a lot of difficulties, viz. considerable energy intensive fractional distillation is required to separate this by-product from the finished product, though formed in a relatively minor quantity, due to its high boiling point as well as its high melting point. For example, phenazine was found to solidify in the upper section of the distillation column due to its high melting point which makes the distillation operation very difficult. Also Phenazine is not desirable in the finished product. Further, methods for decreasing the formation of phenazine have not been addressed in the prior art.

Another objective of the present invention is to achieve better stability of TMAH under the continuous process conditions than that reported earlier and to carry out the coupling reaction without a limitation on the water to base molar ratio at the end of the coupling reaction or in the product of the coupling reaction as stated in the earlier patents, so as to harness the full advantage of carrying out the coupling reaction in continuous manner. TMAH stability in the presence of water is documented in the literature (See e.g. W. Kenneth Musker; J. Chem. Edn., vol. 45, pp. 200-202, (1968) and W. Kenneth Musker; J. Am. Chem. Soc., vol. 86, pp. 960-961 (1964)).

A further objective of the present invention is to optimize the water to "free TMAH" or "unbound TMAH" molar ratio, rather than the water to total base (free TMAH+all other TMA salts including TMA salts of 4-NODPA & 4-NDPA) molar ratio in the product of the coupling reaction in order to minimize the decomposition of TMAH.

None of the prior art patents addresses how to carry out the coupling reaction with high efficiency using a minimal charge of TMAH so that without affecting coupling reaction efficiency, negligible free (unreacted) TMAH remains, thus substantially reducing TMAH decomposition at the end of the coupling reaction even when the water to base molar ratio is very low.

The other objective of the invention is to achieve high productivity by carrying out the coupling reaction in a continuous manner in continuous flow reactors with minimal TMAH decomposition even when the water to total base molar ratio is significantly below 0.6:1.

SUMMARY OF THE INVENTION

Accordingly, in brief summary, one embodiment of the present invention is a process which comprises one or more of the steps of:
i) reacting aniline and nitrobenzene in the presence of water and TMAH as a base, in a continuous manner by feeding the reactants to a series of continuous flow reactors, while continuously distilling off an aniline-water mixture under reduced pressure such that the water to total base molar ratio is less than 0.6:1 at the flow reactors outlet, and the water to unbound TMAH molar ratio is about 4:1 in the reaction product of the coupling reaction, to thereby produce 4-nitrodiphenylamine and/or 4-nitrosodiphenylamine and/or salts thereof;
ii) adding water and hydrogenating the reaction product from step i) in the presence of a suitable hydrogenation catalyst to produce a 4-ADPA-containing reaction product;
iii) separating the hydrogenation catalyst from the reaction mixture to obtain an aqueous phase containing the base catalyst, and an organic phase containing 4-ADPA as the major component; and optionally recycling the recovered hydrogenation catalyst used in step ii) and
iv) separating the organic phase from the aqueous phase and subsequently purifying the organic phase to isolate 4-ADPA and recover excess aniline for recycle in step i), and also recycling the aqueous phase containing the regenerated TMAH to step i) after optional further purification.

Other embodiments of the present invention encompass methods for enhancing the stability of TMAH in aniline and/or in the coupling reaction mixture using different water contents and process conditions.

In other embodiments of the present invention, reductive alkylation of 4-ADPA made from the continuous process is carried out after suitable purification of the 4-ADPA. The reductive alkylation step can be employed for production of commercial antiozonants such as 6-PPD.

DETAILED DESCRIPTION OF THE INVENTION

In a first aspect, the present invention is directed to a continuous process for making 4-ADPA that is economically attractive. More particularly, in a first embodiment the invention provides a process in which TMAH, excess aniline and the hydrogenation catalyst are recycled in a manner which makes the process economically attractive. It has been found that the TMAH and the aniline can be recycled with a minimum loss of reactivity for coupling of aniline with nitrobenzene and that the hydrogenation catalyst can be recycled with a minimum loss of reactivity for hydrogenation, by controlling the level of impurities in the recycle streams and by carefully controlling the amount of water in relation to the base during the reaction steps.

The inventors have found that a larger amount of phenazine forms when the coupling reaction is carried out in a batch process, where nitrobenzene was added in a controlled manner, as compared to a continuous process, since the objective of the batch process was to convert all the nitrobenzene. Based on this objective, the reaction time is fixed and the production of a larger amount of phenazine necessarily results. A reduction of the batch reaction time may not reduce the impurity level due to: a) the availability of pool of reactants in the batch reactor and b) the continuous change in the concentrations of the reactants over time which necessarily occurs in a batch reaction. Both of these conditions are absent in a continuous process.

Carrying out the coupling reaction in a continuous manner resulted in nearly 50% less formation of phenazine and, due to the inherent nature of a continuous process the concentrations of the reactants remained constant thereby providing a highly predictable reaction. In a continuous process the contact time between the raw materials can be altered by changing the feed rate of one or more reactants to the continuous flow reactors in order to reduce the degree of formation of impurities such as phenazine. Thus, the combination of using a continuous process and selection of appropriate feed rates can be used to avoid or reduce the need for elaborate and energy intensive separation steps subsequent to the coupling reaction.

Based on the above-mentioned advantages of the continuous process it has been found that significant improvements can be achieved by adoption of a series of continuous flow reactors. This process design concept provides extensive flexibility in varying process parameters namely reaction rate, raw material feed rate, heat input, reaction pressure, ratios of raw materials etc. It was observed that phenazine can be reduced by 50% in a continuous process as compared to the amount formed in the prior art batch process. This also results in a lower conversion (e.g. <95%) of nitrobenzene to the desired product as compared to the batch process and relatively more formation of azobenzene by-product, which can be converted to aniline and recycled to the process without loss of raw material efficiency. The continuous process also provides flexibility to recover some of the recyclable raw materials at the reaction stage without loading the subsequent hydrogenation stage with unnecessary materials. Lower residence time at particular moisture contents, as well as control of the charge of TMAH, also reduces TMAH degradation which is not possible in the batch process due to requirement of a fixed reaction time and the relatively longer period required for reactor unloading after coupling reaction.

A study of the distillate of the reaction of Example A of the present application was carried out and it was found that the distillate of different reaction mixtures under low pressure as well as under atmospheric pressure, contained varying compositions of aniline—water. This study demonstrates that the aniline-water mixture is distilled as a mere mixture based on their respective mole fractions and relative volatility and not as an azeotrope as previously thought in the prior art. The results of this study are shown in Table 2 of Example A.

On reproducing Example 13 of the '111 patent (Example B) and the similar Example 1 of the '538 patent several times, it was found that the water to base (base is considered as per the definition given in the '111 and '538 patents) molar ratio at the end of the coupling reaction is always more than 0.6 (actually ~1.2 to 1.3). See Table 3 of Example D below.

Example 6 of the '538 patent highlighted that whenever the water to base molar ratio at the end of the coupling reaction goes below 0.6:1 there is substantial base decomposition. However, on repeating this Example 6 (Column 15, lines 19-67 and Table 2 at column 16, lines 1-10 of the '538 patent), it is found that water to base molar ratio remains at about 1.1-1.2 and never goes below 1, since virtually no distillation occurs once this ratio is achieved under the specified reaction conditions (temperature 75° C. and pressure 57 mm of Hg), even by extending the hold period to 4 hrs. TMAH decomposition at the end of nitrobenzene addition as well as at the end of the hold period was comparable and was only up to about 1% or less (Example D, Table 3 below). Total Base in reaction mass after coupling reaction, is analyzed by titration method and method showed ~1% variation and hence to understand the extent of decomposition of TMAH, N-methyl aniline formation was measured by HPLC which, although not equivalent, showed extent of TMAH decomposition in reaction mass. In all the experiments in Table-3, results showed N-methyl aniline formation varying within a narrow range of low value, indicating relatively negligible decomposition, which complemented the less decomposition of TMAH in the reaction product at the end of coupling reaction. It was found that the water content in the reaction mass can only be reduced when the pressure is further reduced to 10-15 mm of Hg pressure and that the TMAH decomposition is much less than that mentioned in Table 2 of Example 6 of the '538 patent.

Further, holding a thermally unstable compound (TMAH) for prolonged reaction time at higher temperature and without reduction of pressure by implementing a hold period beyond 30 minutes in a batch process does not make sense if TMAH decomposition is a primary consideration. There is a major limitation when the reaction is carried out in a batch manner in a large volume reactor, i.e. the hydrostatic head of the liquid increases the overall boiling point of the reaction mass, thereby limiting distillation. In all the aforementioned working examples of the '111 and '538 patents, the initial TMAH to nitrobenzene molar ratio is 1.05 and hence there is always some free (unbound) TMAH present in the reaction mixture that is susceptible to decomposition, whenever the moisture content of the reaction mixture drops below a certain value. This free TMAH and the decomposition thereof has not been adequately addressed in the prior art.

The present inventors have found that TMAH is relatively stable in the presence of aniline and water, particularly at a water to TMAH mole ratio of about 4:1 and that TMAH decomposition occurs when this ratio is reduced to 3.5:1 or less, with concomitant formation of a proportional amount of N-methyl aniline which results from the decomposition of TMAH in the presence of aniline, as shown in Table 4 below. The TMAH decomposition can be decreased by reducing the hold period. As shown in the working examples, the stability of TMAH in the presence of aniline was evaluated by stage-wise distillation of water from a mixture of aqueous TMAH (35% w/w) in aniline to obtain a water to TMAH molar ratio of about 4:1, then about 3.5:1 and then about 3:1, successively at 75° C. under 55 mm Hg pressure (similar to the process conditions mentioned in the first TMAH concentration step of Example 13 of the '111 patent as well as Example 1 of the '538 patent) and subsequently maintaining the reaction mass under atmospheric pressure for a hold period of 4 hours The results shown in Example 2, Table 4 and also FIG. 1 indicate that at water to TMAH molar ratio of about 4:1 and about 3.5:1, N-methyl aniline formation is <500 ppm while at a water to TMAH ratio of about 3:1, TMAH decomposition is up to 1000 ppm at the end of the 4 hour hold period. At the end of a 4 hour hold period, TMAH decomposition was found to be less than 2% for water to TMAH molar ratios of 4:1 and 3.5:1, whereas TMAH decomposition was 3.6% for water to TMAH molar ratio of 3:1. The proportional N-methyl aniline formation with respect to time, confirmed the extent of TMAH decomposition in each case. Therefore, it can be inferred that for any of the above water to TMAH molar ratios, TMAH decomposition can be controlled by reducing the hold time and use of a water to TMAH molar ratio of 4:1 is preferable for better stability.

Also, TMAH 4H$_2$O, TMAH 3.5H$_2$O and TMAH 3H$_2$O were made and added to the same quantity of aniline and held at 80° C. for 4 hours under atmospheric pressure and the TMAH decomposition was evaluated by analyzing TMAH and N-methyl aniline. The results are summarized in Example E, Tables 5-6. It was found that TMAH solutions with an initial water to TMAH molar ratio of about 4:1 and about 3.4:1 were fairly stable in the presence of aniline at about 80° C. for up to 4 hours of hold time, which finding was also supported by the measured quantity of N-methyl aniline formation. However, TMAH decomposition increases as the water to TMAH molar ratio decreases to about 2.9:1 which resulted in a considerable increase in N-methyl aniline content.

Also, solid TMAH.4H$_2$O and TMAH.3H$_2$O were individually heated in the presence of aniline at 80° C. and the evolved vapor was analyzed by a Headspace GC analyzer. The details of these studies on thermal stability of TMAH in aniline are narrated in the working examples given below. The results are given in Example F, Tables 7-8. The results show that N-methyl aniline formed which indicates that TMAH decomposition occurred. N-methyl aniline formation is relatively higher for the sample having a water to TMAH molar ratio of about 3:1 than for the sample with a water to TMAH ratio of about 4:1. This relatively higher decomposition of TMAH at a water to TMAH molar ratio of about 3:1 is also supported by measurement of trimethylamine gas by GC analysis, which gets formed during TMAH decomposition.

All these studies reveal that TMAH is fairly stable when the water to TMAH molar ratio is about 4 and that the rate of TMAH decomposition increases as the water to TMAH molar ratio is lowered to about 3.5 and that the TMAH decomposition significantly increases in the presence of a water to TMAH molar ratio of about 3:1.

The products of the aniline-nitrobenzene coupling reaction carried out in the presence of TMAH are known to include a mixture of TMA salts of 4-NODPA and 4-NDPA and some by-products like azobenzene and phenazine. Thus, tetramethyl cation is stoichiometrically bound at the end of the coupling reaction to 4-NODPA and 4-NDPA. It is found that, at the end of the coupling reaction, depending upon the conversion and selectivity based on nitrobenzene and the moles of TMAH added with respect to the moles of nitrobenzene, some TMAH may remain "free" or "unbound", i.e. some TMAH may remain that is not bound in salts of 4-NODPA or 4-NDPA. For example, in the case of Example 13 of the '111 patent, which employs a TMAH to nitrobenzene molar ratio of 1.05 and may exhibit about a 94% selectivity of nitrobenzene to TMA salts of 4-NODPA+4-NDPA, the free TMAH at the end of reaction works out to be ~0.11 mole.

The present inventors have surprisingly found that the free TMAH, which is present in the reaction product of the coupling reaction at the flow reactors outlet, has an important bearing on the total decomposition of TMAH. Studies of the coupling reaction showed that the decomposition of TMAH can be reduced as long as about 3.5 to 4 moles of water or preferably 4 or more moles of water are present in the reaction mass with respect to the amount of free TMAH remaining in the reaction mass in the reaction product of the coupling reaction. Contrary to the findings of Example 6 of '538 patent, the present inventors have found that water to base molar ratio can be reduced to below 0.6:1 without a significant change in TMAH decomposition. The inventors have found that this can be effectuated by continuing the reaction up to completion of nitrobenzene addition, followed by a 30 minute hold period and then reducing the pressure to 10-15 mm of Hg at 75° C. to effect further distillation and thereby reduce the water to base molar ratio to below 0.6. The results surprisingly show negligible decomposition of TMAH (<1%) and are confirmed by estimation of N-methyl aniline formation in the reaction (See Example D, Table 3 below).

As shown in experiment no. 4 of Table 3, by carrying out an experiment similar to example 13 of the '111 patent and further reducing the pressure, more water can be distilled out of the reaction mass until about 3.5 to 4 moles water remains with respect to the amount of free TMAH in the reaction mixture, which works out to be water to base molar ratio of about 0.38 to 0.44 (found to be 0.42 in experiment 4 of Table 3), since only 0.11 mole of free TMAH remains in this particular reaction mass in the reaction product of the coupling reaction. According to the '538 patent, the total base in the reactor is to be considered as the amount of free base and/or base included in the 4-nitroso- and/or 4-nitrodiphenylamine salts of TMA. See e.g. col. 5, lines 62-65 of the '538 patent.

Stability studies of TMAH in aniline, as shown in the aforementioned Examples D, E and F also support this finding. This finding is also in agreement with the step of concentrating TMAH in aniline, with a water to TMAH molar ratio of at least about 4:1 at the start of the coupling reaction, without much decomposition under the reaction conditions, as mentioned in the '111 and '538 patents.

The amount of water that should be allowed to remain in the reaction product of the coupling reaction at the flow reactors outlet can thus be determined to be the amount of water required for a molar ratio of water to free or unbound TMAH (i.e. TMAH not bound as salt of 4-NODPA or 4-NDPA) of about 3.5-4:1, thus allowing the overall water to total base (the total of free TMAH and bound TMA salts) molar ratio to be reduced to significantly less than 0.6:1, without decomposition of TMAH.

Further experiments as shown in Example 3, following Example 13 of the '111 patent as well as Example 1 of the '538 patent, were carried out wherein nitrobenzene was added over 3 hours at 55 mm Hg followed by a 30 minute hold period and then subsequently reducing the pressure to about 10-20 mm, whereby the molar ratio of water to the total TMAH fed to the reaction was reduced to about 0.4-0.45, without any significant decomposition of TMAH i.e., <1% (the commercially acceptable level as mentioned in Example 6 of the '538 patent). This result is confirmed by N-methyl aniline estimation in the reaction mass.

Further experiments in Example 3, Table 9, with a lower TMAH charge i.e., lowering the TMAH:nitrobenzene molar ratio fed to the reaction from 1.2:1 as in the prior art examples to as low as 0.9:1, resulted in lower quantities of free TMAH remaining in the reaction product of the coupling reaction and about 4 mole equivalent of water or more, relative to free TMAH were found in the reaction product. Thus, by ensuring a lesser amount of free or unbound TMAH in the reaction product of the coupling reaction, an even lower water to base molar ratio can be achieved without significant TMAH decomposition. For example, an initial nitrobenzene to TMAH molar ratio of 1:1 or less can allow a final molar ratio of water to total base fed to the reaction of less than 0.3:1 while preserving a commercially acceptable level of TMAH decomposition i.e., <1%.

Further experiments were carried out by following example 13 of the '111 patent and by charging less moles of TMAH relative to nitrobenzene i.e., using nitrobenzene:TMAH molar ratios varying between 0.9 to 1:1, and further concentrating the reaction mass at the end of hold period by lowering the pressure (about 10 mm Hg pressure at ~75° C.). The molar ratio of water to total base in the reaction mass was found to be about 0.25-0.45, with negligible TMAH decomposition.

Results of the foregoing experiments are summarized in Example 3, Tables 9-10. It is seen that as the TMAH to nitrobenzene molar ratio decreases, the amount of free TMAH in the reaction product of the coupling reaction is reduced and therefore, a water to base molar ratio of <0.6 can be achieved without much decomposition of TMAH. Also, a small increase in azobenzene formation is seen, as the amount of base with respect to nitrobenzene is decreased.

TMAH decomposition also depends on the residence time at the reaction temperature (~75-80° C.) since TMAH is subject to thermal decomposition. The experiments demonstrate that a continuous process provides a distinct advantage over batch process, since in the continuous process the residence time at high temperature can be reduced as compared to a batch process by using appropriate process equipment such as a continuous plug-flow reactor, especially at the end stage of coupling reaction. This type of device can also be suitably heated in different zones so as to heat the coupling reaction mass under vacuum with efficient heat control. Thus, the coupling reaction can be carried out in a continuous manner with an initial charge of a molar ratio of TMAH to nitrobenzene in the range of 0.85:1 to 1.1:1, or, more preferably, in the range of 0.9:1 to 1:1.

Further, the coupling reaction can be completed in a continuous plug flow reactor under suitable temperature and pressure conditions selected for minimal heat exposure of TMAH. For example, the final stage of the reaction can be conducted at a low pressure in the range of 1-25 mm, or, more preferably, between 1-15 mm while controlling the reaction mass temperature to remain below 80° C. or, more preferably, below about 75° C., in order to ensure minimal decomposition of TMAH and achieve a concentrated reaction mass having a water to TMAH molar ratio less than 0.6:1, preferably less than about 0.4:1. Because of an efficient heat and mass transfer rate, the reaction is easily completed in a continuous manner in a series of reactors and hence better process efficiency, as compared to a batch process, can also be achieved.

The reaction mass may then be sent to a hydrogenation step after mixing with an adequate quantity of water to produce 4-ADPA and regenerate TMAH for recovery and recycle. The coupling reaction mass at the end of concentration step comprises of about 0.5-0.55 weight % phenazine with respect to 4-ADPA equivalent.

Further studies on the coupling reaction of aniline and nitrobenzene in the presence of aqueous TMAH in pilot scale in a continuous manner using a combination of flow reactors reveals distinct advantages in terms of consistency of the process, lower energy consumption, and easy operability. In the final concentration step, while reducing water content, the reaction mass is fed through a continuous plug flow reactor under controlled conditions so as to obtain a concentrated reaction mass with a limited amount of free TMAH and a water to base molar ratio of <0.6, preferably, less than about 0.4 (Example 4).

Also, the coupling reaction goes to completion with only a slight stoichiometric excess of TMAH due to the high rate of mass and heat transfer in the continuous plug flow reactor, which provides another advantage relative to a batch process. Hence, with a slight excess of free TMAH beyond the stoichiometric amount, relative to nitrobenzene feed, not only does the reaction go to completion, but also the reaction mass can be concentrated to achieve the water to base molar ratio much less than 0.6. The concentrated coupling mass can be easily hydrogenated by adding an appropriate quantity of water without any adverse effect on the catalyst efficacy, reaction time, and stability of TMAH in the hydrogenation step. The ability to concentrate the reaction mass reduces the mass throughput in the subsequent steps (i.e. hydrogenation) by removing more of the aniline from the reaction mass than in the prior art batch process, thereby improving process efficiency.

Hence, it is possible to obtain a water to base molar ratio less than 0.6:1 without substantial decomposition of the TMAH base. Relatively, more N-methyl aniline is formed during distillation at the end stage of coupling reaction in the batch process than in the continuous process, due to the higher residence time at higher temperature (~80° C.) since the continuous process in plug flow reactor requires a significantly reduced residence time and thus minimizes TMAH exposure at higher temperature. Moreover, the reaction goes to completion with only a slight excess of TMAH over the stoichiometric requirement due to the high heat and mass transfer rate. Finally, more aniline can be removed by concentration of the coupling reaction mass at the flow reactors outlet, thereby reducing the amount of aniline fed to subsequent steps in the process, thereby increasing process efficiency.

Crude 4-ADPA, obtained by carrying out the coupling reaction in aforementioned continuous manner, followed by hydrogenation after adding adequate water, with subsequent separation of the organic and aqueous phases followed by purification provides a highly efficient process for the manufacture of highly pure 4-ADPA (>99% purity). The purification steps may include, for example, fractional distillation and an azobenzene reduction step. The substantially pure 4-ADPA can then be easily converted to a rubber antiozonant such as 6-PPD and similar antiozonants by well-known reductive alkylation methods using a suitable ketone such as methyl-isobutyl ketone (MIBK).

From the foregoing description, one skilled in the art can ascertain the essential characteristics of this invention and without departing from the spirit and scope thereof can make various changes and modifications of the invention to adapt it to various usages and conditions.

The invention is illustrated by the following examples;

EXAMPLES

Example A

Distillation of Aniline and Water Mixture to Study Formation of any Azeotrope Under the Prior Art Reaction Conditions This example illustrates that distillation of a mixture of aniline and water under the prior art reaction conditions leads to different compositions of aniline and water in the distillate and does not provide a distillate which is an aniline/water azeotrope as taught in the prior art patents related to 4-ADPA production. Different compositions of aniline and water were subjected to distillation at reduced pressure, i.e., 55 torr, as used in the Example 13 of the '111 patent, as well as at atmospheric pressure (about 1 bar). The distillate, up to 20 to 70 volume % of the mixture, was collected in each case in a manner which maintained some quantity of the minor component in the bottoms. The results are shown in Table 2 below:

TABLE 2

Aniline - water mixture distillation study:

| | Feed for Distillation | | | Distillate | | |
|---|---|---|---|---|---|---|
| | Input | Input composition | | Output | Output composition | |
| | Weight Gm | Water % | Aniline % | Weight gm | Water % | Aniline % |
| | | | | | At 55 torr | |
| 1 | 300 | 70 | 30 | 93.45 | 81.2 | 18.8 |
| 2 | 300 | 80 | 20 | 65.39 | 83.7 | 16.3 |
| 3 | 300 | 86.6 | 13.4 | 209.68 | 85.2 | 14.8 |
| 4 | 300 | 90 | 10 | 54.25 | 88.9 | 11.1 |
| | | | | | At 760 torr | |
| 1 | 300 | 81 | 19 | 232.64 | 80.7 | 19.3 |
| 2 | 300 | 86.6 | 13.4 | 217.74 | 83.5 | 16.5 |

Example B

Conventional Coupling Reaction Between Aniline and Nitrobenzene

This example illustrates the results obtained when laboratory experiments were conducted similar to Example 13 of the '111 patent.

The coupling reaction was carried out in a 2 liter glass round bottom flask (RB flask) equipped with a stirrer (½ moon blade Teflon™ stirrer), Dean-Stark condenser, a thermometer, Teflon™ baffle and a dropping funnel for nitrobenzene addition. Initially about 25% aqueous TMAH solution (24.8% w/w, 680.7 gm, 168.8 gm on 100% basis, 1.86 moles) was charged into the RB flask. Water was removed by distillation under reduced pressure at 55 mm Hg to obtain an aqueous TMAH solution of 35% w/w TMAH. During this stage the temperature increased to 50-53° C. Aniline was charged (1003.9 gm, 10.76 moles) into the reactor and the distillation was continued under reduced pressure at 55 mm Hg. Water and aniline were removed by distillation until the molar ratio of water to TMAH was about 4:1. During this process the temperature of the reaction mass increased to 70-73° C.

After attaining the required molar ratio of water to base, nitrobenzene (218.3 gm, 1.77 moles) was added continuously over a period of 180 minutes. During the nitrobenzene addition water and aniline were continuously removed from the reaction mass by distillation under reduced pressure at 55 mm Hg. The reaction mass was maintained at about 75° C./55 mm Hg for 0.5 hour, after completion of nitrobenzene addition. The reaction end point was determined by HPLC analysis by monitoring the conversion of nitrobenzene. The total reaction time was about 5.5 hours and a typical selectivity, determined by HPLC at the end of the hold period at nitrobenzene conversion of 99.95% was 4-NODPA—86.62%, 4-NDPA—5.84%, azobenzene—6.3% and phenazine—1.13%. The moisture content of the reaction mass at the end of the batch was found to be 3.16% by the Dean stark method (and 3.21% by material balance) and the water to total base molar ratio in the reaction mass at the end of the coupling was found to be about 1.22 (by material balance 1.24).

Note 1: HPLC Assay: Reverse phase HPLC was used to analyze the reaction mixtures.

Analytical parameters: Column: 5 Lichrosphere RP-18e 250×4.6 or equivalent

HPLC: Agilent 1200 with DAD coupled with Chemstation Software or equivalent

Mobile phase A: methanol HPLC grade

Mobile phase B: To a solution of 75% (v/v) water and 25% (v/v) methanol add 0.2-0.3 ml/liter of triethyl amine and adjust the pH was adjusted to 6.5 to 7.0 using $H_3PO_4$.

Calculations: Internal standard method

Note 2: Dean Stark method: The material to be tested was heated under reflux with water immiscible solvent, which co-distils with water. A mixture of water and the solvent separates on condensing the vapors; the heavier water layer was collected in a graduated receiving tube, the solvent running back into the flask. From the amount of water collected, moisture content calculations were done.

Example C

Reduction of the Coupling Reaction Product

This example illustrates reduction of 4-NODPA and 4-NDPA in the coupling mass.

In a 2 liter capacity autoclave was placed the coupling reaction mass at the end of the coupling reaction (900 gm) containing aniline (54%), 4-NODPA (25%), 4-NDPA (1.8%) (Both 4-NODPA and 4-NDPA exist in salt form), phenazine (0.3%), azobenzene (1.8%) and total TMAH (13.5%) (total TMAH includes both free TMAH and TMAH in salt form). All percentages are weight percentages. To this product was added water (307 gm) and noble metal catalyst (e.g. 5% Pd/C). The reaction mixture was heated at 80° C. under a hydrogen pressure of 15 kg/cm². At the end of reduction (no hydrogen absorption, typically 30 minutes) the remaining 4-NODPA and 4-NDPA content was almost nil. HPLC gives 4-ADPA analysis which corresponds to at least 98 mole % of 4-NDPA and 4-NODPA.

The reaction mass was filtered to separate hydrogenation catalyst, followed by separation of the organic and aqueous phases. The aqueous phase comprising TMAH and traces of organics was purified by hydrocarbon solvent extraction and other purification steps, followed by concentration to regenerate TMAH suitable for recycle. The organic phase was suitably washed with fresh water to remove any traces of TMAH, followed by as several purification steps namely fractional distillation and reduction under suitable process conditions to produce highly pure 4-ADPA.

Examples 1 and D

This Example Repeats Example 6 of the '538 Patent to Study the Decomposition of the Base (TMAH) as a Function of the Water to Total Base Molar Ratio at the End of the Coupling Reaction and after a Hold Period This example illustrates the effect of the hold period at the end of the coupling reaction on the water to total base molar ratio and TMAH decomposition to determine whether a water to base molar ratio below 0.6:1 can be obtained simply by holding the reaction mass for a given number of hours (Example D). It also illustrates the effect of a water to total base molar ratio below 0.6:1 on the TMAH decomposition, by adjusting the reaction conditions at the end of coupling reaction (Example 1).

For Example D, three different experiments were conducted following the procedure given in Example 6 of U.S. Pat. No. 6,140,538, wherein nitrobenzene was added in 2 hours, 2.5 hours and 3 hours, each followed by a 4 hour hold period at 75° C. and 57 mm Hg pressure (equivalent to 76 mbar).

In a typical reaction, the coupling reaction was carried out in a 2 liter glass round bottom flask (RB flask) equipped with a stirrer (½ moon blade Teflon™ stirrer), a thermometer, a baffle and a dropping funnel for nitrobenzene addition. Initially, an aqueous solution of TMAH (35.01% w/w, 485.66 gm, 170.03 gm on 100% basis, 1.87 moles) was charged into the RB flask. Aniline was then charged (995.92 gm, 10.68 moles) into the RB flask and distillation was continued under reduced pressure at 57 mm Hg. Water and aniline mixture was removed by distillation until the molar ratio of water to total TMAH was about 4:1. During this process the temperature of the reaction mass increased to 70-73° C.

After attaining the required molar ratio of water to total base, nitrobenzene (218.99 gm, 1.78 moles) was added continuously over a given period i.e. 120 or 150 or 180 minutes. During the nitrobenzene addition, water and aniline were continuously removed from the reaction by distillation under reduced pressure at 57 mm Hg. The reaction mass was maintained at about 75° C./57 mm Hg for 4 hours after completion of nitrobenzene addition.

The reaction mass was analyzed at the end of nitrobenzene addition and at the end of the hold period for nitrobenzene conversion by HPLC analysis. Also, the reaction mass was analyzed for TMAH content, N-methyl aniline, and moisture by titration, HPLC & Dean Stark techniques, respectively.

In another experiment (Example 1), nitrobenzene was added over a period 2 hours as above, followed by a 0.5 hour hold period by keeping the reaction temperature at 75° C. and the pressure at 57 mm Hg. Distillation of the aniline and water mixture was then continued at ~75° C. by decreasing the pressure gradually to about 15 mm Hg, so as to be able to obtain a water to total base molar ratio below 0.6. The reaction mass was analyzed for nitrobenzene conversion by HPLC analysis. Also, the reaction mass was analyzed for TMAH content, N-methyl aniline and moisture by titration, HPLC & Dean Stark techniques, respectively (Table 3)

TABLE 3

| Exp. No. | Details | W/B molar ratio - at the end of NB addition | | TMAH Accountability (%) | N-Me aniline in the reaction mass at the end of nitrobenzene addition (ppm) | W/B molar ratio - at the end of reaction (NB addition + 4 hrs hold) | | TMAH Accountability (%) | N-me aniline in the reaction mass at the end of reaction (NB addition + 4 hrs hold) (ppm) |
|---|---|---|---|---|---|---|---|---|---|
| | | M.B. | D.S. | | | M.B. | D.S. | | |
| 1 | 2 hr NB Addn. + 4 hr hold | 1.77 | 1.72 | 100.4 | 6 | 1.14 | 1.16 | 99.30 | 85 |
| 2 | 2.5 hr NB Addn. + 4 hr hold | 1.76 | 1.75 | 100 | 5 | 1.27 | 1.30 | 100.32 | 71 |
| 3 | 3 hr NB Addn. + 4 hr hold | 1.69 | 1.62 | 100.6 | 16 | 1.14 | 1.17 | 100.6 | 58 |
| 4 | 2 hr NB Addn. + 0.5 hr hold + up to 15 mm hg | 1.47 | 1.56 | 100.4 | 20 | 0.33 | 0.42 | 99.8 | 329 |

M.B. = Material balance;
D.S. = Dean Stark method;
N-Me aniline = N-Methyl aniline Example 2

TMAH Stability, in the Presence of Aniline, Wherein Different Water to Total TMAH Molar Ratios were Obtained by Distilling Excess Water This example illustrates the effect of water to TMAH molar ratio on TMAH stability in the presence of aniline and also the effect of a hold period at elevated temperature on TMAH stability for certain water to total TMAH molar ratios.

Experiments were conducted wherein aqueous TMAH along with aniline is concentrated by continuously distilling off an aniline and water mixture under reduced pressure so as to reach water to total base molar ratios of about 4:1, 3.5:1 and 3:1. After obtaining the specified water to total base molar ratio, the reaction mixture was held for 4 hours and was analyzed every hour for TMAH and N-methyl aniline contents.

In a typical reaction, TMAH was concentrated in the presence of aniline in a 2 liter Glass Round Bottom flask (RB flask) equipped with a stirrer (½ moon blade Teflon™ stirrer), a thermometer, a baffle, and a dropping funnel for aniline addition. Initially an aqueous solution of TMAH (34.63% w/w, 491.27 gm, 170.13 gm on 100% basis, 1.87 moles) was charged into the RB flask. Aniline (1004.11 gm, 10.80 moles) was charged into the reactor and the distillation was continued under reduced pressure at 55 mm Hg. Water and aniline mixture was removed by distillation until a given initial molar ratio of water to TMAH was obtained. During this process the temperature of the reaction mass increased to 70-73° C.

Figure 1:
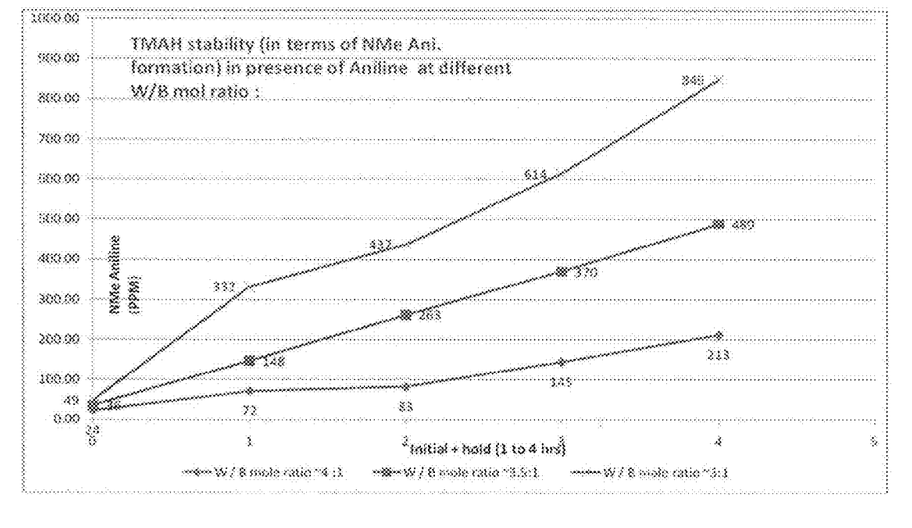

After attaining the required initial water to base molar ratio, the reaction mass was kept on hold at about 75° C. for 4 hrs. The reaction mixture was analyzed for TMAH content and for N-methyl aniline, as an indicator of the extent of TMAH decomposition, and the distillate was analyzed for water content. Results are summarized in Table 4. Also FIG. 1 depicts the increase in N-methyl aniline formation with time at different water to total base molar ratios.

TABLE 4

| Exp. No. | Water/Base molar ratio at the end of TMAH concentration | TMAH decomposition at the end of 4 hrs hold (%) | N-methyl aniline in the reaction mass (ppm) during hold Hold (hrs) | | | | |
|---|---|---|---|---|---|---|---|
| | | | 0 | 1 | 2 | 3 | 4 |
| 1 | 4.08 | 1.6 | 24 | 72 | 83 | 145 | 213 |
| 2 | 3.53 | 1.0 | 36 | 148 | 263 | 370 | 489 |
| 3 | 3.15 | 3.6 | 49 | 332 | 437 | 614 | 849 |

Example E

Stability of Solid TMAH in Aniline Having Varying Water Contents at 80° C. For Different Hold Times This example illustrates stability of solid TMAH at different water to total TMAH molar ratios, in aniline solvent and also the effect of hold period on solid TMAH stability for the given water to total TMAH molar ratio.

Aqueous TMAH (~35% w/w) was concentrated by continuously distilling and water under reduced pressure so as to reach water to total base molar ratios of about 4:1, 3.5:1 and 3:1. The TMAH samples thus prepared were heated to about 80° C. in aniline and held up to 4 hours at atmospheric pressure under a nitrogen blanket. Samples were analyzed every hour for TMAH and N-methyl aniline. The results are summarized in Tables 5 and 6.

TABLE 5

Compositions of aniline-TMAH mixtures

| Sr. No. | Sample | Aniline (gm) | TMAH (gm) molar ratio-water to TMAH = 4.07:1 | TMAH (gm) molar ratio-water to TMAH = 3.38:1 | TMAH (gm) molar ratio-water to TMAH = 2.86:1 |
|---|---|---|---|---|---|
| 1 | Sample 1 | 151.3 | 47.1 | — | — |
| 2 | Sample 2 | 147.3 | — | 42.0 | — |
| 3 | Sample 3 | 143.7 | — | — | 39.77 |

TABLE 6

TMAH decomposition over time in terms of N-methyl aniline formation

| Sample | Water/Base molar ratio at the end of TMAH concentration | TMAH accountability at the end of 4 hours hold (%) | N-methyl aniline in the reaction mass (ppm) during hold Hold (hrs) 0 | 1 | 2 | 3 | 4 |
|---|---|---|---|---|---|---|---|
| Sample 1 | 4.11 | About 100 | 1 | 2 | 15 | 25 | 44 |
| Sample 2 | 3.45 | 99.35 | 1 | 153 | 285 | 368 | 424 |
| Sample 3 | 2.90 | 94.2 | 906 | 1012 | 1191 | 1245 | 1375 |

Example F

TMAH Stability in Aniline, Wherein a TMAH Solid Having Varying Water Contents is Heated in Aniline This example illustrates the stability of TMAH at different water to total base (TMAH) molar ratios in the presence of aniline.

TMAH samples with water to base (TMAH) molar ratios of about 4:1 and about 3:1 were prepared from and aqueous solution containing about 35% w/w of TMAH by distillation of water under reduced pressure. These samples were heated at about 80° C. in the presence of aniline for up to 2 hours in a closed system and analyzed for TMAH decomposition products, namely, trimethyl amine and N-methyl aniline. The results are summarized in Tables 7 and 8.

TABLE 7

Compositions of aniline-TMAH mixtures

| Sample | Aniline (gm) | TMAH (gm) Water:total TMAH molar ratio = 4.08:1 | TMAH (gm) Water:TMAH molar ratio = 3.17:1 |
|---|---|---|---|
| Sample 1 | 3.96 | 1.13 | — |
| Sample 2 | 4.01 | 1.13 | — |
| Sample 3 | 4.20 | — | 1.15 |
| Sample 4 | 4.07 | — | 1.13 |

TABLE 8

TMAH decomposition over time in terms of trimethylamine and N-methyl aniline formation

| | | TMAH (molar ratio with water) 4.08:1 | | TMAH (molar ratio with water) 3.17:1 | |
|---|---|---|---|---|---|
| Sr. No. | Details | Sample 1 Hold (1 hr) | Sample 2 Hold (2 hrs) | Sample 3 Hold (1 hr) | Sample 4 Hold (2 hrs) |
| 1 | trimethylamine (relative ratio)* | 1 | 1.47 | 1.65 | 1.79 |
| 2 | N-methyl aniline (ppm) | 22 | 40 | 146 | 359 |

*= Value obtained by GC area % is taken as unity for comparison.

Example 3

Coupling Reaction of Aniline with Nitrobenzene

This example illustrates the effect of different molar ratios of total base (TMAH) to nitrobenzene fed to the coupling reaction on the decomposition of TMAH at the end of coupling reaction when the water to total base molar ratio is well below 0.6.

The coupling reaction was carried out in a 2 liter Glass Round Bottom flask (RB flask) equipped with a stirrer (½ moon blade Teflon™ stirrer), a thermometer, a baffle, and a dropping funnel for nitrobenzene addition. Initially, an aqueous solution of TMAH (35.65% w/w, 475.16 gm, 169.39 gm on 100% basis, 1.86 moles) was charged into the RB flask. Aniline was charged (1005.4 gm, 10.81 moles) into the reactor and distillation was continued under reduced pressure at 55 mm Hg. A water and aniline mixture was removed by distillation until the molar ratio of water to TMAH was about 4:1. During this process the temperature of the reaction mass increased to 70-73° C.

After attaining the required molar ratio of water to total base for the start of the coupling reaction, nitrobenzene (218.82 gm., 1.78 moles) was added continuously over a period of 180 minutes. During nitrobenzene addition, water and aniline were continuously removed from the reaction by distillation under reduced pressure at 55 mm Hg. The reaction mass was maintained at about 75° C./55 mm Hg for 0.5 hour, after completion of nitrobenzene addition (entry no. 6, Tables 9 and 10).

Distillation of the aniline and water mixture was continued at about 75° C. by decreasing the pressure gradually to about 15 mm Hg so as to obtain a water to total base molar ratio below 0.6:1. The reaction mass was analyzed for nitrobenzene conversion by HPLC analysis. The reaction mass was also analyzed for TMAH content, N-methyl aniline content and moisture content by titration, HPLC and Dean Stark techniques, respectively. The results are summarized in Tables 9 and 10 (entry nos. 1 to 5).

TABLE 9

| Exp. No. | AN:NB:TMAH (molar ratio) | NB conversion (%) | Water/total base molar ratio - at the end of the coupling reaction (NB addition + hold) | | Water/Free TMAH molar ratio - at the end of the coupling reaction (NB addition + hold) | | TMAH Accountability (%) | N-methyl aniline in the reaction mass at the end of coupling reaction (ppm) | Free TMAH at the end of coupling reaction (% of input) based on selectivity |
|---|---|---|---|---|---|---|---|---|---|
| | | | M.B. | D.S. | M.B. | D.S. | | | |
| 1 | 6.06:1:1.21 | 99.83 | 0.49 | 0.57 | 1.94 | 2.26 | 93.94 | 6000 | 23.18 |
| 2 | 6.05:1:1.05 | 99.83 | 0.45 | 0.40 | 4.01 | 3.62 | 99.1 | 711 | 9.86 |
| 3 | 6.05:1:1.0 | 99.81 | 0.33 | 0.38 | 3.90 | 4.37 | 99.40 | 427 | 7.58 |
| 4 | 6.06:1:0.95 | 99.71 | 0.34 | 0.26 | 10.1 | 7.80 | 98.75 | 178 | 3.50 |
| 5 | 6.06:1:0.90 | 99.07 | 0.20 | 0.21 | Practically no free TMAH | | 99.13 | 56 | Negligible |
| 6 | 6:1:0.90 | 96.08 | 1.29 | 1.33 | 71.4 | 73.89 | 99.16 | 65 | 1.80 |

M.B. = material balance;
D.S. = Dean Stark method

TABLE 10

| Exp. no. | AN:NB:TMAH (molar ratio) | Free TMAH at the end of coupling reaction (% on input) based on selectivity | Free and bound TMAH based on input moles | | % molar selectivity of azobenzene based on NB Input (HPLC) Azobenzene |
|---|---|---|---|---|---|
| | | | Free TMAH moles | Bound TMAH | |
| 1 | 6.06:1:1.21 | 23.18 | 0.278 | 0.932 | 6.04 |
| 2 | 6.05:1:1.05 | 9.86 | 0.10 | 0.95 | 5.99 |
| 3 | 6.05:1:1.0 | 7.58 | 0.076 | 0.924 | 6.78 |
| 4 | 6.06:1:0.95 | 3.50 | 0.03 | 0.92 | 6.63 |
| 5 | 6.06:1:0.90 | Negligible | — | about 0.90 | 7.26 |
| 6 | 6:1:0.90 | 1..80 | 0.02 | 0.88 | 6.87 |

Example 4

Coupling Aniline with Nitrobenzene in Continuous Manner

This example illustrates the coupling reaction of aniline with nitrobenzene carried out in a continuous manner to obtain a reaction mass having a negligible presence of nitrobenzene with a water to total base molar ratio less than 0.6 and without substantial decomposition of TMAH.

a) In a typical pilot plant run aniline (35.86 kg/hr), nitrobenzene (5.93 kg/hr) and TMAH (35% w/w) (11.34 kg/hr) were fed to a pre-mixer, followed by passing through a series of continuous flow reactors at about 50 mm Hg. The temperature of the reaction mass progressively increased from about 65° C. in the pre-mixer to about 80° C. with distillation of aniline and water from the flowing reaction mass. The last reactor in the series was a continuous plug flow reactor, which was maintained at 10 mm Hg and the reaction mass was passed through this continuous plug flow reactor in a continuous manner with distillation of aniline and water. The temperature of the bottom mass was about 75° C. The output was about 34 kg/hr with a negligible presence of nitrobenzene. Typical selectivity based on nitrobenzene added was about 90% for the total of 4-NODPA and 4-NDPA, azobenzene about 9.2%, and phenazine about 0.5%. The moisture content was around 0.85% w/w by the Dean-Stark method and the TMAH content by analysis around 11.6% w/w giving a water to total base molar ratio of about 0.37. The N-methyl aniline content was around 19 ppm. Thus, it was possible to reduce the water to total base molar ratio to less than 0.6 without appreciable decomposition of TMAH base.

b) The reaction mass fed to the continuous plug flow reactor was separately distilled to study the effect of batch distillation on conversion and impurities formation. In a 1 liter 4-neck round bottom flask, 750 gm feed of the flow reactor mass (obtained from an intermediate step of pilot scale experiment as in a) above) was taken and heated to 75° C. under agitation. The pressure was reduced gradually to about 10 mm Hg and distillation of an aniline-water mixture was continued to complete the reaction as determined by the point when no nitrobenzene remains unreacted. The water to base molar ratio becomes less than 0.6 as a result of this distillation. At the end of distillation, typical selectivity based on nitrobenzene was 4-NODPA+4-NDPA about 89.5%, azobenzene about 9.7%, and phenazine about 0.5%. The moisture content was around 0.59% w/w by the Dean-Stark method and TMAH content was about 10.57% w/w giving a water to total base molar ratio of about 0.28. The N-methyl aniline content was around 130 ppm, indicating significantly higher TMAH decomposition in comparison to the concentration step a) carried out in a continuous plug flow reactor.

The invention claimed is:

1. A process comprising the step of:
reacting aniline and nitrobenzene in the presence of TMAH as base and water in a continuous manner employing a series of continuous flow reactors under conditions that produce at the flow reactors outlet a coupling reaction product including one or more TMA-salts of 4-NODPA and 4-NDPA along with one or more by-products including at least azobenzene, wherein a water to free TMAH molar ratio in the reaction product is at least about 3:1 and a water to total base ratio in the reaction product is less than 0.6:1.

2. The process according to claim 1 further comprising the step of adding water to the reaction product and then hydrogenating the reaction product with the added water in the presence of suitable hydrogenation catalyst to produce a 4-ADPA-containing reaction product.

3. The process according to claim 2, further comprising the steps of:

separating the hydrogenation catalyst from the reaction mixture to obtain an aqueous phase containing base catalyst and an organic phase containing at least 4-ADPA, azobenzene and phenazine;

purifying the organic phase under suitable conditions to obtain 4ADPA and recover excess aniline which is recycled as a reactant to the coupling step of the process; and purifying the aqueous phase to regenerate TMAH base for recycle to the coupling step of the process.

4. The process according to claim 1, wherein a molar ratio of water to total TMAH is up to 10:1 at the start of the coupling reaction of aniline with nitrobenzene.

5. The process according to claim 1, wherein in the coupling step, an initial molar ratio of aniline to nitrobenzene is from 6:1 to 15:1.

6. The process according to claim 1, wherein in the coupling step, an initial molar ratio of aniline to nitrobenzene is from 6:1 to 10:1.

7. The process according to claim 1, wherein in the coupling step, an initial molar ratio of total TMAH to nitrobenzene is from 0.8:1 to 1.1:1.

8. The process according to claim 1, wherein in the coupling step an initial molar ratio of total TMAH to nitrobenzene is from 0.85:1 to 1:1.

9. The process according to claim 1, wherein the coupling step is carried out in a combination of one or more continuous stirred tank reactors and one or more continuous plug flow reactors to effect coupling of aniline with nitrobenzene.

10. The process according to claim 1, wherein the last stage of the coupling step is carried out in a plug flow reactor.

11. The process according to claim 1, wherein in the reaction product of the coupling step, the water to free TMAH molar ratio is at least about 3.5:1.

12. The process according to claim 1, wherein the coupling step is carried out at a pressure of from 1 to 60 mm of Hg.

13. The process according to claim 1, wherein the coupling step is carried out at a temperature in a range of 60-80° C.

14. The process according to claim 2, wherein the reaction product plus water for the hydrogenation step contains 20 to 50 wt. % of water, relative to total mass upon initiation of hydrogenation.

15. The process according to claim 3, wherein recovered hydrogenated catalyst is recycled to the hydrogenation step.

16. The process according to claim 3, wherein the aqueous phase containing TMAH catalyst is used to form a subsequent reaction mixture for use in the coupling step.

17. The process according to claim 14, wherein organic phase is suitably purified to obtain substantially pure 4-ADPA.

18. The process according to claim 17, further comprising the step of reductively alkylating 4-ADPA with at least one ketone.

19. The process according to claim 1, wherein the molar ratio of water to total TMAH base in the reaction product is less than about 0.45:1.

20. The process according to claim 1, wherein the molar ratio of water to total TMAH base in the reaction product is less than about 0.3:1.

21. The process according to claim 1, wherein the nitrobenzene conversion to 4-NODPA and 4-NDPA in the reaction product is less than 95%.

22. The process according to claim 1, wherein in the reaction product of the coupling step, the water to free TMAH molar ratio is at least about 4:1.

23. The process according to claim 3, further comprising the steps of converting azobenzene to aniline and recycling this aniline to the coupling reaction.

* * * * *